United States Patent [19]

Flanagan et al.

[11] Patent Number: 5,093,105
[45] Date of Patent: Mar. 3, 1992

[54] RADIOPHARMACEUTICAL BACTERIOSTATS

[75] Inventors: Richard J. Flanagan, St. Lazare; Daniel Tartaglia, Anjou, both of Canada

[73] Assignee: Merck Frosst Canada, Inc., Quebec, Canada

[21] Appl. No.: 682,170

[22] Filed: Apr. 9, 1991

[51] Int. Cl.$^5$ .............................................. A61K 49/02
[52] U.S. Cl. ..................................... 424/1.1; 252/625
[58] Field of Search ........................... 424/1.1; 252/625

[56] References Cited

FOREIGN PATENT DOCUMENTS

| | | |
|---|---|---|
| 0193372 | 9/1986 | European Pat. Off. . |
| 0306984 | 3/1989 | European Pat. Off. . |
| 62/153217 | 7/1987 | Japan . |
| 2127689 | 4/1984 | United Kingdom . |

OTHER PUBLICATIONS

Abdullah, M. J. and Said, S. A., *Drug Res.*, 31 (I), Nr. 1 (1981), pp. 59–61.
Richards, R. M. E. and McBride, R. J., *J. Pharm. Pharmac.* 24, 145–148, (1972).
Kurtz, L. D. (I), *Chemical Abstracts*, 76, 103785 h (1972).
Kurtz, L. D. (II), *Chemical Abstracts*, 76, 10378k (1972).
*Remington's Pharmaceutical Sciences*, 18th ed., Philadelphia College of Pharm. Sci., (1990) p.1164.
*Remington's Pharmaceutical Sciences*, 18th ed., Philadelphia Collge of Pharm. Sci. (1990), p. 1170.

*Primary Examiner*—John S. Maples
*Attorney, Agent, or Firm*—Joseph F. DiPrima; William H. Nicholson; J. Eric Thies

[57] ABSTRACT

Benzalkonium chloride and benzethonium chloride are each useful in radiopharmaceutical preparations as bacteriostatic agents which are compatible with anti-oxidants.

24 Claims, No Drawings

RADIOPHARMACEUTICAL BACTERIOSTATS

SUMMARY OF THE INVENTION

The present invention is related to the use of benzalkonium chloride or benzethonium chloride as bacteriostatic agents in radiopharmaceutical preparations.

This invention also relates to radiopharmaceutical compositions comprising benzalkonium chloride or benzethonium chloride and a radiopharmaceutical agent.

BRIEF DESCRIPTION OF DISCLOSURES IN THE ART

Benzalkonium chloride has been widely used as a preservative for pharmaceutical preparations, especially in ophthalmic, dermatologic, gynecological and dental applications. For example, a European Patent Application (EPO Publication No. 0,306,984) and a publication (J. Pharm. Pharmac., 1972, 24, 145-148) describe the use of benzalkonium chloride in ophthalmic formulations. Benzalkonium chloride may also be utilized in a composition for the cleaning and storage of contact lenses (see U.S. Pat. No. 3,882,036 and Japanese Patent Application JP 62/153217). Benzalkonium chloride has also been used as a preservative for pharmaceutical compositions for nasal administration (see EPO Publication No. 0,193,372 and UK Patent Application GB 2,127,689A).

Benzethonium chloride may be utilized in similar applications. Due to its low water solubility, benzethonium chloride has been primarily utilized in antiperspirant and deodorant sticks.

BACKGROUND OF THE INVENTION

Noninvasive, nuclear imaging techniques can be used to obtain basic and diagnostic information about the physiology and biochemistry of a variety of living subjects including experimental animals, normal humans, and patients. These techniques rely on the use of sophisticated imaging instrumentation which is capable of detecting radiation emitted from radiotracers administered to such living subjects. The information obtained can be reconstructed to provide planar and tomographic images which reveal the distribution of the radiotracer as a function of time. Use of appropriately designed radiotracers can result in images which contain information on structure (low resolution), function, and most importantly, physiology and biochemistry of the subject. Much of this information cannot be obtained by any other means. The radiotracers used in these studies are designed to have defined behaviors in vivo which permit the determination of specific information concerning the physiology or biochemistry of the subject or of the effect that various diseases or drugs have on the physiology or biochemistry of the subject. Currently, radiotracers are available for obtaining useful information concerning such things as cardiac function, myocardial blood flow, lung perfusion, bone density, liver function, kidney function, brain blood flow, regional brain glucose, and oxygen metabolism.

A variety of radiotracers have been proposed for radioimaging including compounds labeled with either positron or gamma emitting nuclides. For imaging, the most commonly used positron emitting radiotracers are $^{11}C$, $^{18}F$, $^{15}O$, and $^{13}N$, all of which are accelerator produced, and have half-lives of 20, 110, 10, and 2 min respectively. Since the half-lives of these radionuclides are so short, it is only feasible to use them at institutions which have an accelerator on site for their production, limiting their use to approximately 25 medical centers in the U.S. and only about 50 throughout the world. Several gamma emitting radiotracers are available which can be used by essentially any hospital in the U.S. and in most hospitals throughout the world. The most widely used of these are $^{99m}Tc$ (Tc-99m), $^{201}Tl$, $^{123}I$ and $^{131}I$. $^{201}Tl$ is a monovalent cation which is used for measuring myocardial blood flow. Both $^{99m}Tc$ and $^{131}I$ can be incorporated into a variety of radiotracers and are widely used in most modern hospitals. $^{99m}Tc$ is generator produced, has a 6 hour half-life, and emits a 140 keV gamma photon which makes this radionuclide nearly ideal for use with current planar and single photon emission computerized tomography (SPECT) cameras. $^{99m}Tc$ is a transition metal which forms a wide variety of complexes with molecules containing coordinating ligands (e.g. molecules with free thiol, amine, carboxyl or phosphonate functional groups). $^{99m}Tc$ labeled compounds have been developed for many diagnostic imaging applications, such as functional studies (e.g. cardiac, renal, liver) and perfusion studies (e.g. myocardial, brain, lung, bone).

Diagnostic imaging kits which employ technetium-99m generally comprise several components, i.e. a source of Tc-99m, a ligand, a reducing agent and an antioxidant. The diagnostic agent is generally formed by reacting Tc-99m in an oxidized state with an appropriate ligand in the presence of a reducing agent under conditions which allow formation of a stable complex between Tc-99m in a reduced state (e.g., III, IV or V valence state) and the ligand. The complex should have the desired property of becoming localized in the target organ upon introduction into a patient. Additionally, an antioxidant may be present to suppress the formation of unwanted impurities from the reduction.

To facilitate handling and storage, the aforementioned components of $^{99m}Tc$-based imaging kits are generally kept in a freeze-dried state prior to reconstitution. Such lyophilized components may packaged individually or in various combinations as warranted by the specific application. Prior to administration the components of the kit are reconstituted by the addition of sodium pertechnetate in saline and mixing, if separately packaged. The shelf life of lyophilized $^{99m}Tc$-based radiopharmaceuticals prior to reconstitution may be as long as 12 to 18 months. Upon reconstitution, however, the shelf life is only 6 hours. Because many hospitals generally make up a single large batch of injection solution, the short post-reconstitution shelf life imposes serious constraints on efficient management of diagnostic procedures.

Such a short post-reconstitution shelf life is due to regulations concerning bacterial growth in the parenteral solutions. Although a wide variety of antibacterial agents are known in the art, very few have been utilized in radiopharmaceutical preparations. This is primarily due to their incompatibility with antioxidants. For example methylparaben and propylparaben are utilized as antibacterial agents in commercially available $^{99m}Tc$-based radiopharmaceuticals. Because they are incompatible with the antioxidant employed in the composition, the concentration of $^{99m}Tc$ complex must be kept low to avoid the formation of undesireable by-products. The $^{99m}Tc$-based by-products diminish the quality and resolution of diagnostic imaging. Other bacteriostats, including phenol, thymol, benzyl alcohol, and phenylethyl alcohol, are similarly imcompatible with antioxidants.

Benzalkonium chloride is known as a topical antiinfective, antiseptic and antimicrobial agent. Benzalkonium chloride is bacteriostatic in low and bactericidal in high concentrations. Gram-positive bacteria are more sensitive than gram-negative bacteria. Benzalkonium chloride is used for application to skin and mucous membranes. It is widely used in over-the-counter ophthalmic solutions and in compositions for cleaning and storing contact lenses. It is also used for the sterilization of inanimate articles, such as surgical instruments. For a review of the antimicrobial activity and use of benzalkonium chloride see W. Gump, "Disinfectants and Antiseptics" in Kirk-Othmer *Encyclopedia of Chemical Technology*, Vol. 7 (Wiley-Interscience, New York, 3rd. ed; 1979) pp. 815-818.

Benzethonium chloride has similar properties, but, due to its low water solubility, it is primarily utilized for cosmetic applications and in antiperspirant and deodorant sticks.

As noted earlier, all current Tc-99m radiopharmaceuticals require the addition of an anti-oxidant and a bacteriostat to extend shelf life post reconstitution. Presently, bacteriostats are seldom used because they interfere with most anti-oxidants and thus the shelf life is limited by regulations to six hours.

Accordingly, an object of the present invention is to provide a bacteriostatic agent for radiopharmaceutical preparations which is compatible with anti-oxidants.

It has now been surprisingly found that radiopharmaceutical compositions can be obtained wherein both bacterial growth and oxidation are minimized. The present invention has met this need by being compatible with current anti-oxidants, allowing the extension of the shelf life up to 24 hours post reconstitution.

DETAILED DESCRIPTION OF THE INVENTION

The present invention is directed to radiopharmaceutical compositions comprising:
(a) a $^{99m}$Tc-based radiopharmaceutical;
(b) a water-soluble pertechnetate reducing agent;
(c) a radical-scavenging antioxidant; and
(d) a bacteriostat selected from:
 (i) benzalkonium chloride, and
 (ii) benzethonium chloride.

The present invention is also directed to methods of utilizing radiopharmaceutical formulations comprising:
(a) a $^{99m}$Tc-based radiopharmaceutical;
(b) a water-soluble pertechnetate reducing agent;
(c) a radical-scavenging antioxidant; and
(d) a bacteriostat selected from:
 (i) benzalkonium chloride, and
 (ii) benzethonium chloride for diagnostic imaging (including bone scintigraphy, kidney radioimaging, lung radioimaging, brain radioimaging, and blood pool and myocardial infarct radioimaging).

As used herein, a "$^{99m}$Tc-based radiopharmaceutical" is a complex of $^{99m}$Tc in the III, IV or V oxidation state with an organic ligand(s). Such radiopharmaceutical may be pre-formed prior to combination with other ingredients or may be formed in situ.

The source of Tc-99m should preferably be water soluble. Preferred sources are alkali and alkaline earth metal salts of pertechnetate (TcO$_4^-$) such as, for example, sodium pertechnetate. Tc-99m is most preferably obtained in the form of fresh sodium pertechnetate from a sterile Tc-99m generator (e.g., from a conventional $^{99}$Mo/$^{99m}$Tc generator). Any other source of physiologically acceptable Tc-99m may be used.

Tc-99m in the form of pertechnetate can be used in amounts up to about 200 mCi/ml, preferably between about 20-200 mCi/ml.

The ligand or chelating agent for $^{99m}$Tc which is selected will vary with the desired diagnostic imaging application. Such ligand should complex quickly with $^{99m}$Tc to form a stable, biologically acceptable complex.

For the preparation of kits for bone scintigraphy, the preferred $^{99m}$Tc ligand is a diphosphonic acid, pyrophosphate or trimetaphosphate. For the preparation of kits for bone scintigraphy it is even more preferred that the diphosphonic acid be selected from: methylenediphosphonic acid (MDP), hydroxymethylene-diphosphonic acid (HMDP), ethane-1-hydroxy-1,1-diphosphonic acid (EHDP), 1-hydroxypropane-1,1-diphosphonic acid, 2,3-dicarboxypropane-1,1-diphosphonic acid, pyrophosphate or trimetaphosphate.

For the preparation of kits for radioimaging of the kidney, the preferred $^{99m}$Tc ligand is selected from: diethylenetriaminepentaacetic acid (pentetate) (N,N-bis[2-[bis(carboxymethyl)amino]ethyl]-glycine), 2,3-dimercaptosuccinic acid (DMSA), glycero-glucoheptanoic acid, or N-[N-[N-(mercaptoacetyl)glycyl]-glycyl]glycine.

For the preparation of kits for radioimaging of the lung, the preferred $^{99m}$Tc ligand is selected from: macroaggregated albumin (MAA), aggregated human albumin, albumin colloid, or recombinant human albumin/human serum albumin in microspherical form.

For the preparation of kits for blood pool and myocardial infarct imaging, the preferred $^{99m}$Tc ligand is selected from: iminodiphosphonic acid, [(acac)$_2$en], hydrophosphonic acid, glyceroglucoheptanoic acid, a monoclonal antibody (MAb), especially a monoclonal antibody to fibrin or to myosin, tissue plasminogen activator (tPA), 1-isocyano-2-methoxy-2-methylpropane (sestamibi), or [tris(1,2-cyclohexanedionedioximato)-O]-methylborane (teboroxime).

For the preparation of kits for brain/cerebral perfusion imaging the preferred $^{99m}$Tc ligand is selected from: diethylenetriamine pentaacetic acid, [tris(2,3-butanedione-dioximato)-O]-(2-methylpropyl)borane (siboroxime), ethyl cystinate dimer (neurolyte), or 3,3'-[(2,2-dimethyltrimethylene)diimino]di-2-butanone-dioxime (exametazime).

For the preparation of kits for radioimaging of the liver, gall bladder, and/or spleen the preferred $^{99m}$Tc ligand is selected from: N-[2-[(3-bromo-2,4,6-trimethylphenyl)amino]-2-oxoethyl]-N-(carboxymethyl)-glycine (mebrofenin), N-[2-[[2,6-bis(1-methylethyl)phenyl]amino]-2-oxoethyl]-N-(carboxymethyl)-glycine (disofenin), N-(carboxymethyl)-N-[2-[2,6-dimethylphenyl)-amino]-2-oxoethyl]glycine (lidofenin), or polyisohexylcyanoacrylate nanoparticles.

For the preparation of kits for radioimaging of tumors in breast, colorectal, ovarian, pancreatic, prostate, small-cell lung, and/or non-small-cell lung cancers and non-Hodgkin's lymphoma the preferred $^{99m}$Tc ligand is selected from: a monoclonal antibody (MAb), especially a monoclonal antibody selected from the group consisting of: LS2D617, NR-LU-10, 28A32, 703D4 (ATCC HB 8301), 704A1 (ATCC HB 8302), murine IgG1 monoclonal antibody BTMA8, or a monoclonal antibody from a human myeloma cell line.

The amount of the ligand may range from about 0.5 mg/ml up to the amount maximally soluble or suspendable in the medium.

The pharmaceutically acceptable salts of the radiopharmaceuticals include the conventional non-toxic formed, e.g., from non-toxic inorganic or organic acids or bases. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicyclic, sulfanilic, 2-acetoxybenzoic, fumaric, toluenesulfonic, methanesulfonic, ethanedisulfonic, oxalic, isethionic, and the like. Base salts include ammonium salts, alkali metal salts such as sodium and potassium salts, alkaline earth metal salts such as calcium an magnesium salts, salts with organic basis such as dicyclohexylamine salts, N-methyl-D-glucamine, and salts with amino acids such as arginine, lysine, and so forth.

The "radical scavenging antioxidant" is an organic compound which prevents or inhibits the re-oxidation of reduced technetium-99m to pertechnetate (Tc VII) by diminishing the effect of dissolved oxygen in the formulation. Suitable radical scavenging antioxidants include para-aminobenzoic acid (PABA), gentisic acid, and ascorbic acid. The radical scavenging antioxidant is generally present in amounts of about 0.01–10 mg/ml.

Reducing agents must be physiologically acceptable and effective for reducing technetium-99m from its oxidized state to the III, IV or V oxidation state. In the present invention, the choice of reducing agent is not critical, but it is preferred that it be water-soluble. As used herein the term "pertechnetate reducing agent" is intended to include compounds, complexes, or the like, comprising a reducing ion capable of reducing heptavalent technetium ($TcO_4^-$) to trivalent, tetravalent and-/or pentavalent technetium. Free metals such as tin are also known for use as pertechnetate reducing agent. Thus, it is more convenient to use metal compounds which provide the reducing metal cation in soluble form. Examples of suitable water-soluble reducing agents are stannous chloride, stannous fluoride, stannous tartrate, and sodium dithionite. The preferred agents are stannous reducing agents, such as stannous chloride and stannous fluoride. The most preferred agent is stannous chloride.

The amount of reducing agent used is the amount necessary to reduce the technetium to provide for binding to the ligand in a reduced state. In a preferred mode, stannous chloride ($SnCl_2$) is the reducing agent, and the concentration may range between about 1–5000 μg/ml, preferably between about 30–500 μg/ml.

As used herein the term "bacteriostat" includes chemical agents which inhibit bacterial growth. At higher concentrations the instant compositions exhibit bacteriolytic activity (i.e. cause the destruction or dissolution of bacterial cells) and/or bacteriocidal activity (i.e. kill bacteria). Such compositions and utilities are also encompassed within the scope of the instant invention.

Apart from applications to $^{99m}Tc$-based radiopharmaceuticals, the present invention has utility in all radiopharmaceuticals which require reconstitution. Additionally, the present invention contemplates benzalkonium chloride or benzethonium chloride as a bacteriocide in radiopharmaceutical solutions which do not require reconstitution, especially those comprising a radiohalogen, in particular $^{123}I$ or $^{131}I$.

Accordingly, an alternate embodiment of the present invention is directed to radiopharmaceutical composition comprising:
(a) a radioactive iodine-based radiopharmaceutical;
(b) an autoradiolytic decomposition-inhibiting antioxidant selected from:
  (i) ascorbic acid
  (ii) nicotinamide,
  (iii) nicotinic acid, and
  (iv) a mixture of acorbic acid and nicotinamide;
(c) a bacteriostat selected from:
  (i) benzalkonium chloride, and
  (ii) benzethonium chloride.

The alternate embodiment of the present invention is also directed to methods of utilizing radiopharmaceutical formulations comprising:
(a) a radioactive iodine-based radiopharmaceutical;
(b) an autoradiolytic decomposition-inhibiting antioxidant selected from:
  (i) ascorbic acid
  (ii) nicotinamide,
  (iii) nicotinic acid, and
  (iv) a mixture of acorbic acid and nicotinamide;
(c) a bacteriostat selected from:
  (i) benzalkonium chloride, and
  (ii) benzethonium chloride
for diagnostic imaging (including bone scintigraphy, kidney radioimaging, lung radioimaging, brain radioimaging, and blood pool and mycardial infarct radioimaging).

As used herein, a "radioactive iodine-based radiopharmaceutical" is a radiotracer wherein $^{122}I$, $^{123}I$, $^{125}I$ or $^{131}I$ is incorporated into an organic or inorganic molecule.

For the preparation of radiopharmaceutical formulations for diagnostic imaging it is preferred that the radioactive iodine-based radiopharmaceutical is selected from the group consisting of: [$^{123}I$], [$^{125}I$], or [$^{131}I$]-N-[2-iodo-benzoyl]-glycine (ortho-iodohippurate); [$^{131}I$]N,N,N'-trimethyl-N'-(2-hydroxy-3-methyl-5-iodobenzyl)-1,3-propanediamine; [$^{123}I$]1,3-dihydro-3-(4-iodobenzoylamino)-1-methyl-5-phenyl-2H-1,4-benzodiazepin-2-one; [$^{123}I$]N-(2,3-dihydro-1-methyl-2-oxo-5-phenyl-1H-1,4-benzoiazepin-3-yl)-N'-(3-iodophenyl)urea; [$^{123}I$]4-iodo-alphamethyl-N-(1-methylethyl)benzeneethanamine; [$^{131}I$]-19-iodo-cholest-5-en-3β-ol; [$^{123}I$] or [$^{131}I$]-6-iodo-cholest-5-en-3β-ol; [$^{123}I$] or [$^{131}I$]-m-iodobenzylguanidine; [$^{123}I$] or [$^{131}I$]-p-iodo-N-isopropyl-amphetamine; [$^{123}I$] or [$^{131}I$]-3-iodo-2-hydroxy-6-methoxy-N-[(1-ethyl-2-pyrrolidinyl)methyl]benzamide; [$^{123}I$] or [$^{131}I$]-9-(3,3-diethylureido)-4,6,6a,7,8,9-hexahydro-7-methyl-2'-ioddoindolo[4,3-f,g]quinoline (iodo-lisuride); [$^{123}I$] or [$^{131}I$]-N-(8-benzyl-1αα,5αH-nortropan-3β-yl)2,3-dimethoxy-4-iodo-benzylamide (iodo-tropapride); [$^{123}I$] or [$^{131}I$]-N-(2-diethylaminoethyl)-4-iodobenzamide.

As used herein, an "autoradiolytic decomposition-inhibiting antioxidant" is an organic compound which diminishes the chemical breakdown of the radiopharmaceutical induced by radioactive decay of the radioactive species itself. Suitable autoradiolytic decomposition inhibiting antioxidants including ascorbic acid, nitotinamide, nicotinic acid, or combinations thereof.

The use of such antioxidants is described in U.S. Pat. No. 4,880,615. These compounds retard the radiolytic decompositon caused by radioactive decay of iodine thereby prolonging their useful shelf-life. The autoradiolytic decomposition inhibiting antioxidant is generally present in amounts of about 0.01-20 mg/ml.

Although both benzalkonium chloride (BAC) and benzethonium chloride (BEC) have utility in the present invention, benzalkonium chloride is preferred. Benzalkonium chloride (N-alkylbenzyldimethylammonium chloride and/or N-dialkylbenzylmethylammonium chloride) (C.A.S. Registry No. 8001-54-5) is commercially available, or may be prepared by methods well known in the art.

Benzalkonium chloride is a mixture of N-alkylbenzyldimethylammonium chlorides of the general formula $[C_6H_5CH_2N(CH_3)_2R]Cl$, in which R represents a mixture of alkyls, including all or some of the group beginning with $n\text{---}C_8H_{17}$ and extending through higher homologs of $n\text{---}C_{20}H_{41}$, with $n\text{---}C_{12}H_{25}$, $n\text{---}C_{14}H_{29}$ and $n\text{---}C_{16}H_{33}$ comprising the major portion. In general, on the anhydrous basis, the content of $n\text{---}C_{12}H_{25}$ homolog is not less than 30%, and the content of the $n\text{---}C_{14}H_{29}$ homolog is not less than 10%, of the total alkylbenzyldimethyl-ammonium chloride content. The amounts of the $n\text{---}C_{12}H_{25}$ and $n\text{---}C_{14}H_{29}$ homolog components generally comprise together not less than 50% of the total alkylbenzyldimethylammonium chloride content. Also contemplated within the scope of the present invention are benzalkonium chloride species of the general formula $[C_6H_5CH_2N(CH_3)RR]Cl$, in which R is independently as defined above. Such N-alkyldimethylbenzylammonium chloride and N-dialkylmethylbenzylammonium chloride species may be present individually or together in a ratio of 10:1 to 1:10. Commercially available benzalkonium chloride may comprise N-alkyldimethylbenzylammonium chlorides alone, or may additionally comprise N-dialkylmethylbenzylammonium chlorides in the aforementioned ratios.

Although it is preferred that the benzalkonium species be in the chloride salt form (i.e. benzalkonium chloride), other salt forms are also contemplated within the scope of the instant invention, with the bromide, iodide, acetate, benzoate, sulfonate, benzenesulfonate, and phosphonate being exemplary.

The $^{99m}Tc$-based radioactive diagnostic agent or the non-radioactive carrier therefore may be formulated in a lyophilized composition, a simple powdery composition, an aqueous solution or the like. In addition to the said essential components, it may contain any conventional additive, such as a pH-adjusting agent and an isotonizing agent (e.g. sodium chloride).

The radioiodine-based radioactive diagnostic agent or the non-radioactive carrier therefore is generally formulated in an aqueous solution. In addition to the said essential components, it may contain any conventional additive, such as a pH-adjusting agent and an isotonizing agent (e.g. sodium chloride).

For diagnostic imaging in a subject the radiopharmaceutical compositions of the present invention may be adminstered by intravenous, oral, or nebular administration. For bone scintigraphy in a subject, intravenous administration is preferred. For radioimaging of the kidney in a subject, intravenous administration is preferred. For radioimaging of the lung in a subject, intravenous or nebular admministration is preferred. For radioimaging of blood pool and myocardial infarct in a subject, intravenous administration is preferred. For radioimaging of the brain in a subject, intravenous administration is preferred. For radioimaging of the liver, gall bladder, and/or spleen in a subject, intravenous administration is preferred. For radioimaging of tumors in a subject, intravenous administration is preferred.

The concentration of the bacteriostat in the instant radiopharmaceutical compositions will vary with a variety of factors including the $^{99m}Tc$-based radiopharmaceutical, the pertechnetate reducing agent, and the antioxidant employed, temperature and time of storage, and the specific diagnostic application. For benzalkonium chloride the concentration is preferably from about 0.00001% to about 0.01% (w/v), and more preferably from about 0.00005% to about 0.001% (w/v), and even more preferably from about 0.001% to about 0.0005% (w/v). For benzethonium chloride the concentration is preferably from about 0.00001% to about 0.01% (w/v), and more preferably from about 0.00005% to about 0.001% (w/v), and even more preferably from about 0.0001% to about 0.0005% (w/v).

Similarly, the concentration of the bacteriostat in the radiopharmaceutical compositions of the alternate embodiment of the present invention will vary with a variety of factors including the radioiodine-based radiopharmaceutical, the autoradiolytic decomposition-inhibiting antioxidant employed, temperature and time of storage, and the specific diagnostic application. For benzalkonium chloride the concentration is preferably from about 0.00001% to about 0.01% (w/v), and more preferably from about 0.00005% to about 0.001% (w/v). For benzethonium chloride the concentration is preferably from about 0.00001% to about 0.01% (w/v), and more preferably from about 0.00005% to about 0.001% (w/v).

The following examples are given for the purpose of illustrating the present invention and shall not be construed as being limitations on the scope or spirit of the instant invention.

EXAMPLE 1

MDP/PABA with Benzalkonium Chloride as Preservative

A preliminary radiolabelling test of benzalkonium chloride (BAC) with sodium pertechnetate $^{99m}Tc$ in the presence of para-aminobenzoic acid (PABA) was conducted.

Three vials with a total volume of 10 ml from a recently manufactured methylene diphosphonic acid (MDP) kit containing PABA were treated with various amounts of benzalkonium chloride, i.e., 1, 5 and 10 mg which corresponded to 0.01, 0.05 and 0.10% solutions. Radiochromatography was performed using ITLC-SG strips developed in acetone and saline. The vials were tested at 5 and 24 hours post reconstitution. At these two periods, less than 1% free pertechnetate and reduced hydrolyzed technetium was found in the three vials.

This test demonstrated that benzalkonium chloride did not have a deteriorating effect on PABA nor on the physical appearance of the product (no precipitate was observed). Hence, BAC does not interfere with the anti-oxidant properties of PABA. In contrast, benzethonium chloride caused the phosphonate to precipitate giving a cloudy solution. Benzethonium chloride, similarly, did not interfere with the anti-oxidant properties of PABA.

EXAMPLE 2

MDP/PABA Formulated with Benzalkonium Chloride-Stress Test

Four vials of MDP/PABA were reconstituted with 500 mCi of pertechnetate $^{99m}$Tc in 9 mL of normal saline. Immediately to two vials were added 1 mg/1 mL (0.01%) of benzalkonium chloride solution. Similarly, to the remaining two vials we added 10 mg/1 mL (0.1%). The radiochromatography tests as described in Example 1 were performed at 5 and 24 hours post reconstitution (PR):

| | Percent of free $^{99m}$Tc Pertechnetate | | | |
|---|---|---|---|---|
| | 0.01% | | 0.1% | |
| Time PR | #1 | #2 | #3 | #4 |
| 5 hrs | 1.8 | 1.5 | 1.0 | 1.2 |
| 24 hrs | <1 | <1 | <1 | <1 |

The above data shows that even 10 mg of benzalkonium chloride added with 500 mCi pertechnetate $^{99m}$Tc did not affect the stability of the product. The four solutions remained clear with no sign of precipitate up to 48 hours post labelling. Thus, even under strenuous conditions and in the presence of BAC, the antioxidant properties of PABA are maintained.

EXAMPLE 3

MDP/PABA Compared with MDP/PABA/BAC-BIODISTRIBUTION STRESS TEST

A lyophilized batch of MDP/PABA formulated with benzalkonium chloride (MDP/PABA/BAC) was prepared and tested. The bacterial preservative was added prior to freeze-drying. No special precaution was taken in order to avoid excessive air oxidation of the [tin].

A side by side study of biodistribution of the two formulations with and without benzalkonium chloride was conducted.

A radiochemical "stress test" was also performed on three vials of MDP/PABA/BAC. A "non-stressed" vial was tested simultaneously as a control.

Each lyophilized vial contained 10 mg of MDP, 1 mg of stannous chloride dihydrate, 2 mg of PABA and 50 μg of benzalkonium chloride (BAC). The pH was adjusted to 7.0. When the benzalkonium chloride was added to the final solution, a slight haze appeared. The haze was filtered off to give a clear solution.

A. BIOLOGICAL DATA

The dosage was 83 μg MDP per rat (130–150 g). Tissue distribution was monitored at 20 minutes, 1 hour, 2 hours, 6 hours and 24 hours post-reconstitution (PR).

As shown by the following data, the biodistribution of the radiopharmaceutical was not altered by the addition of BAC.

1. Blood elimination.

The elimination pattern was very similar for both formulations. No significant difference was seen between the two formulations.

2. Liver elimination.

The liver elimination was slightly faster at first for MDP/PABA/BAC, and approximately the same after three hours post injection.

3. Kidney uptake.

The kidney uptake and elimination was the same for both preparations.

4. Stomach and Proximal Intestine.

The stomach and proximal intestine also showed the same elimination pattern. No significant difference between the two preparations.

5. Muscle uptake.

The muscle activity was the same for both preparations.

6. Bone uptake.

The total bone uptake was a few percent lower for the benzalkonium formulation. The observed difference was probably insignificant, and was due to the general variability of bone uptake. This was not enough to make a real difference on bone scintigraphy.

| | Percent of Injected Dose Recovered | | | |
|---|---|---|---|---|
| ORGAN | ANI-MAL #1 | ANI-MAL #2 | ANI-MAL #3 | MEAN |
| MDP/PABA | (20 Min PR) | | | |
| BLOOD | 3.9 | 3.3 | 3.0 | 3.4 |
| LIVER | 1.1 | 0.7 | 1.3 | 1.0 |
| KIDNEYS | 2.5 | 4.3 | 1.5 | 2.8 |
| STOMACH + PI | 0.6 | 1.4 | 0.8 | 0.9 |
| MUSCLE | 6.2 | 3.9 | 4.0 | 4.7 |
| BONE | 58.6 | 48.6 | 53.2 | 53.4 |
| MDP/PABA | (1 Hr PR) | | | |
| BLOOD | 0.3 | 0.3 | 0.3 | 0.3 |
| LIVER | 0.3 | 0.6 | 0.5 | 0.5 |
| KIDNEYS | 0.7 | 0.8 | 0.9 | 0.8 |
| STOMACH + PI | 0.2 | 0.1 | 0.1 | 0.1 |
| MUSCLE | 0.5 | 0.6 | 0.5 | 0.1 |
| BONE | 65.6 | 64.5 | 63.8 | 64.8 |
| MDP/PABA | (3 Hr PR) | | | |
| BLOOD | 0.1 | 0.1 | 0.1 | 0.1 |
| LIVER | 0.1 | 0.1 | 0.1 | 0.1 |
| KIDNEYS | 0.5 | 0.1 | 0.4 | 0.3 |
| STOMACH + PI | 0.1 | 0.1 | 0.1 | 0.1 |
| MUSCLE | 0.7 | 0.6 | 0.6 | 0.7 |
| BONE | 45.6 | 48.0 | 48.6 | 47.4 |
| MDP/PABA | (6 Hr PR) | | | |
| BLOOD | 0.1 | 0.1 | 0.1 | 0.1 |
| LIVER | 0.1 | 0.1 | 0.1 | 0.1 |
| KIDNEYS | 0.5 | 0.6 | 0.5 | 0.5 |
| STOMACH + PI | 0.1 | 0.1 | 0.1 | 0.1 |
| MUSCLE | 0 | 0 | 0 | 0 |
| BONE | 55.0 | 54.5 | 49.4 | 53.0 |
| MDP/PABA | (24 Hr PR) | | | |
| BLOOD | 0.1 | 0.1 | 0.1 | 0.1 |
| LIVER | 0.2 | 0.4 | 0.4 | 0.3 |
| KIDNEYS | 0.5 | 0.8 | 0.7 | 0.7 |
| STOMACH + PI | 0.02 | 0.02 | 0.02 | 0.02 |
| MUSCLE | 0.2 | 3.5 | 0.2 | 1.3 |
| BONE | 60.6 | 63.8 | 71.4 | 65.2 |
| MDP/PABA/BAC | (20 Min PR) | | | |
| BLOOD | 2.1 | 1.7 | 2.5 | 2.1 |
| LIVER | 0.5 | 0.3 | 0.4 | 0.4 |
| KIDNEYS | 1.1 | 2.2 | 1.2 | 1.5 |
| STOMACH + PI | 0.3 | 0.2 | 0.3 | 0.3 |
| MUSCLE | 2.3 | 0.1 | 0.7 | 1.0 |
| BONE | 49.3 | 43.2 | 54.2 | 48.9 |
| MDP/PABA/BAC | (1 Hr PR) | | | |
| BLOOD | 0.3 | 0.3 | 0.3 | 0.3 |
| LIVER | 0.1 | 0.1 | 0.1 | 0.1 |
| KIDNEYS | 0.5 | 0.5 | 0.9 | 0.6 |
| STOMACH + PI | 0.2 | 0.2 | 0.2 | 0.2 |
| MUSCLE | 0.6 | 0.5 | 0.5 | 0.5 |
| BONE | 59.4 | 57.8 | 54.8 | 57.3 |
| MDP/PABA/BAC | (3 Hr PR) | | | |
| BLOOD | 0.2 | 0.1 | 0.1 | 0.1 |
| LIVER | 0.6 | 0.1 | 0.1 | 0.3 |
| KIDNEYS | 0.1 | 0.5 | 0.5 | 0.4 |
| STOMACH + PI | 0.1 | 0.1 | 0.1 | 0.1 |
| MUSCLE | 0.1 | 0.3 | 0.2 | 0.2 |
| BONE | 54.8 | 48.8 | 60.1 | 54.6 |
| MDP/PABA/BAC | (6 Hr PR) | | | |

-continued

| ORGAN | Percent of Injected Dose Recovered | | | |
|---|---|---|---|---|
| | ANI-MAL #1 | ANI-MAL #2 | ANI-MAL #3 | MEAN |
| BLOOD | 0.1 | 0.1 | 0.1 | 0.1 |
| LIVER | 0.1 | 0.1 | 0.1 | 0.1 |
| KIDNEYS | 0.5 | 0.6 | 0.6 | 0.6 |
| STOMACH + PI | 0.1 | 0.3 | 1.2 | 0.5 |
| MUSCLE | 0.1 | 0.1 | 0.1 | 0.1 |
| BONE | 49.1 | 63.5 | 55.0 | 55.9 |
| MDP/PABA/BAC | (24 Hr PR) | | | |
| BLOOD | 0.1 | 0.1 | 0.1 | 0.1 |
| LIVER | 0.1 | 0.1 | 0.1 | 0.1 |
| KIDNEYS | 0.5 | 0.5 | 0.2 | 0.4 |
| STOMACH + PI | 0.1 | 0.1 | 0.1 | 0.1 |
| MUSCLE | 0.2 | 0.4 | 0.3 | 0.3 |
| BONE | 55.0 | 55.9 | 47.5 | 52.8 |

B. RADIOCHEMICAL "STRESS TEST"

Four vials of the lyophilized product were labelled with $^{99m}$Tc-sodium pertechnetate. Each received 500 mCi in 10 mL of technetium from a recent elution. For the first three vials, twenty minutes after reconstitution, 7 mL were removed. The fourth vial remained untouched. The vials were kept at room temperature throughout the length of the experiment.

The radiochemical tests were performed at 0.5, 6.0 and 24 hours post reconstitution. At all times, the unbound pertechnetate remained less than 1%.

EXAMPLE 4

A test of the bacteriostatic effects of various concentrations of benzalkonium chloride in MDP/PABA was conducted. A total of fourteen vials, two each of the six concentrations of benzalkonium chloride in MDP/PABA and two control MDP/PABA vials were utilized. A dilute source of microorganisms was prepared by adding 3 drops of a "dust culture" (which was a mixed culture derived from dust and comprised a variety of wild strains of bacteria and fungi typical to ambient conditions) to 1 liter of sterile water for injection. After sufficient agitation, three drops of the dilute culture were added to one vial of each concentration, including one zero vial, and all fourteen vials were left to incubate overnight (approx. 18 hours) at room temperature. One tube (15 mL) of Fluid Thioglycollate medium and one tube (15 mL) of Tryptic Soy medium was inoculated with 1 milliliter from each of the fourteen incubated vials. Each tube was incubated for fourteen days. At the end of the normal fourteen day incubation period, all sixteen culture tubes representing concentrations of 50 μg and over (those tubes which did not show growth) were inoculated with concentrated "dust culture" to prove their ability to maintain growth at the end of the period.

CONCLUSION

Growth was observed in both media at benzalkonium chloride concentrations of 10 μg and 25 μg per vial, while concentrations of greater than 25 μg per vial and higher produced no growth. All controls showed no growth as expected. The beneficial effect of the benzalkonium chloride was evident in the viability test at concentrations of 250 μg per vial and over.

RESULTS

A - STERILITY TEST

| BAC CONCENTRATION | INOCULATED | | CONTROL | |
|---|---|---|---|---|
| | THIO. | SOY | THIO. | SOY |
| ZERO | POS. 1/18 | POS. 1/22 | NEG. 1/30 | NEG. 1/30 |
| 10 μg | POS. 1/19 | POS. 1/22 | NEG. 1/30 | NEG. 1/30 |
| 25 μg | POS. 1/22 | POS. 1/22 | NEG. 1/30 | NEG. 1/30 |
| 50 μg | NEG. 1/30 | NEG. 1/30 | NEG. 1/30 | NEG. 1/30 |
| 100 μg | NEG. 1/30 | NEG. 1/30 | NEG. 1/30 | NEG. 1/30 |
| 250 μg | NEG. 1/30 | NEG. 1/30 | NEG. 1/30 | NEG. 1/30 |
| 1000 μg | NEG. 1/30 | NEG. 1/30 | NEG. 1/30 | NEG. 1/30 |

B - VIABILITY CHECK

| | DATE GROWTH OBSERVED | |
|---|---|---|
| | THIO | SOY |
| 50 μg control | 2/1 | 2/2 |
| innoc. | 2/1 | 2/2 |
| 100 μg control | 2/1 | 2/2 |
| innoc. | 2/1 | 2/6 |
| 250 μg control | NEG. | NEG. |
| innoc. | NEG. | NEG. |
| 1000 μg control | NEG. | NEG. |
| innoc. | NEG. | NEG. |

EXAMPLE 5

MDP/PABA/BAC Formulation

This test was designed to determine a suitable ratio of $SnCl_2 \cdot 2H_2O$ to benzalkonium chloride that would satisfy the radiochemical "stress test" and still remain clear on reconstitution. It was also desired to produce a solution which would not be colloidal prior to the freeze-drying process.

Four batches of MDP/PABA/BAC kits were prepared, lyophilized, and tested. The formulations were as follows:

1. 10 mg MDP, 1.0 mg $SnCl_2 \cdot 2H_2O$, 2 mg PABA, 50 μg Benzalkonium Cl.
2. 10 mg MDP, 1.0 mg $SnCl_2 \cdot 2H_2O$, 2 mg PABA, 25 μg Benzalkonium Cl.
3. 10 mg MDP, 0.5 mg $SnCl_2 \cdot 2H_2O$, 2 mg PABA, 50 μg Benzalkonium Cl.
4. 10 mg MDP, 0.5 mg $SnCl_2 \cdot 2H_2O$, 2 mg PABA, 25 μg Benzalkonium Cl.

The benzalkonium chloride was added as a dilute solution to the final preparations. Prior to filtration, batch #1 was found to be slightly colloidal. Batch #3 was also colloidal, but to a much lesser degree. Batches #2 and #4, which had less benzalkonium chloride, were visibly clear prior to filtration. All solutions were clear after the final filtration through a 0.22 μm membrane filter. Therefore, the more benzalkonium chloride in solution, the more precipitation observed prior to filtration. Approximately twenty vials of each formulations were lyophilized. The results of testing performed on the final products are as follows:

A. Physical Appearance

Upon reconstitution, batches #1 and #2 were clear. Batch #3 and #4 were slightly colloidal with low volume reconstitution (less than 2 mL). On reconstitution with larger volumes (5 mL or more), batches #3 and #4 were clear. In general, these four formulations were clearer than the MDP/PABA kit vials reconstituted with less than 3 mL per vial. In fact, most of the kits reconstituted with low volume (<3 mL) looked slightly colloidal. Therefore, the benzalkonium chloride may actually make reconstituted vials clearer.

B. Radiochemical "Stress Test"

One vial from each batch was reconstituted with 500 mCi $^{99m}$Tc-sodium pertechnetate in 10 mL. Twenty minutes later, 7 mL were removed. The vials were left at room temperature for the duration of the test. The percent reduced $TcO_2$ was found to be less than 1% for the whole testing period, thus these results were not included in the following table:

| Time | Percent TcO4 | | | |
|---|---|---|---|---|
| | #1 | #2 | #3 | #4 |
| 0.5 Hr P-R | <1 | <1 | <1 | <1 |
| 3.0 Hr P-R | <1 | <1 | <1 | <1 |
| 6.0 Hr P-R | <1 | <1 | <1 | <1 |
| 24 Hr P-R | <1 | 1.9 | 77.8 | 84.2 |

(P-R = Post-Reconstitution)

C. Biological Test

For each batch, three adult rats were injected, and sacrificed one hour later. The results are expressed, below, as the mean ± the standard deviation:

| ORGAN | Percent of Injected Dose (Dosage was 83 μg/0.5 mL) | | | |
|---|---|---|---|---|
| | #1 | #2 | #3 | #4 |
| BLOOD | 0.6(0.2) | 0.4(0.1) | 0.2(0.1) | 0.5(0.2) |
| LIVER | 0.2(0.1) | 0.2(0.1) | 0.2(0.0) | 0.2(0.0) |
| KIDNEYS | 0.7(0.1) | 0.8(0.3) | 0.9(0.3) | 1.4(1.0) |
| STOMACH + PI | 0.2(0.2) | 0.1(0.0) | 0.2(0.1) | 0.3(0.2) |
| MUSCLE | 0.9(0.2) | 1.0(0.4) | 0.8(0.2) | 0.9(0.3) |
| BONE | 47.6(10.3) | 54.5(9.5) | 59.4(1.8) | 56.7(5.2) |

Conclusion

Physically, batches #1 and #2 which have 1 mg of $SnCl_2 \cdot 2H_2O$ were clearer on reconstitution with low volume than batches #3 and #4 (which have 0.5 mg of $SnCl_2 \cdot 2H_2O$). Batch #1 was slightly cloudy. Batch #2 was the clearest. Batches #3 and #4 were cloudier on reconstitution with low volume, but no more than our regular kits.

The radiochemical "stress test" showed that 0.5 mg of $SnCl_2 \cdot 2H_2O$ was insufficient to maintain efficient labelling up to 24 hours post reconstitution.

The biological tests performed in rats do not show significant differences between these four batches after early reconstitution.

Overall, BAC neither improved nor diminished the reducing capacity of stannous chloride in the radiopharmaceutical formulations.

EXAMPLE 6

A microbiological test was conducted according to USP XXI. The results show that 10 or 25 μg BAC in a volume of 10 ml will provide effective bacteriostasis by inhibiting bacterial, fungal and mold growth.

| Trial 1: MDP Control | | | |
|---|---|---|---|
| Organism | Original Inoculum (cfu/ml) | Dilution Needed | Adjusted Cell Suspension (cfu/ml) |
| Aspergillis niger (ATCC 16404) | 1.80 × 10⁵ | — | 1.80 × 10⁵ |
| Candida albicans (ATCC 10231) | 1.56 × 10⁶ | — | 1.56 × 10⁶ |
| Staphyloccocus aureus (ATCC 6538) | 5.88 × 10⁷ | 1/10 | 5.88 × 10⁶ |

(10 ml volume) (0.1 ml of the adjusted cell suspension were added to each of 20 ml of the product. Product on test was stored at 20° C.)

| Day | | Aspergillis Niger (cfu/ml) | Candida Albicans (cfu/ml) | Staphylococcus Aureus (cfu/ml) |
|---|---|---|---|---|
| 0 | Saline | 1.76 × 10⁵ | 1.76 × 10⁶ | 2.08 × 10⁷ |
| 0 | Sample | 1.60 × 10⁵ | 1.16 × 10⁶ | 1.04 × 10⁷ |
| 7 | Saline | 1.28 × 10⁵ | 6.96 × 10⁵ | 8.0 × 10⁵ |
| 7 | Sample | 1.44 × 10⁵ | 7.12 × 10⁴ | 9.2 × 10⁵ |
| 14 | Saline | 0.96 × 10⁵ | 3.72 × 10⁵ | 0 |
| 14 | Sample | 1.44 × 10⁵ | 2.36 × 10³ | 12 |
| 21 | Saline | 0.84 × 10⁵ | 1.60 × 10⁵ | 0 |
| 21 | Sample | 1.32 × 10⁵ | 4.80 × 10³ | 0 |
| 28 | Saline | 1.08 × 10⁵ | 0.84 × 10⁵ | 0 |
| 28 | Sample | 1.52 × 10⁵ | 3.24 × 10³ | 0 |
| % viable after 28 days | | 95% | 0.28% | 0 |

| Trial 2: MDP + 10 μg BAC | | | |
|---|---|---|---|
| Organism | Original Inoculum (cfu/ml) | Dilution Needed | Adjusted Cell Suspension (cfu/ml) |
| Aspergillis niger (ATCC 16404) | 1.80 × 10⁵ | — | 1.80 × 10⁵ |
| Candida albicans (ATCC 10231) | 1.56 × 10⁶ | — | 1.56 × 10⁶ |
| Staphyloccocus aureus (ATCC 6538) | 5.88 × 10⁷ | 1/10 | 5.88 × 10⁶ |

(10 ml volume) (0.1 ml of the adjusted cell suspension were added to each of 20 ml of the product. Product on test was stored at 20° C.)

| Day | | Aspergillis Niger (cfu/ml) | Candida Albicans (cfu/ml) | Staphylococcus Aureus (cfu/ml) |
|---|---|---|---|---|
| 0 | Saline | 1.76 × 10⁵ | 1.76 × 10⁶ | 2.08 × 10⁷ |
| 0 | Sample | 1.12 × 10⁵ | 1.24 × 10⁶ | 1.40 × 10⁷ |
| 7 | Saline | 1.28 × 10⁵ | 6.96 × 10⁵ | 8.0 × 10⁵ |
| 7 | Sample | 2.44 × 10² | 1.2 × 10³ | 6 |
| 14 | Saline | 0.96 × 10⁵ | 3.72 × 10⁵ | 0 |
| 14 | Sample | 28 | 2.72 × 10² | 0 |
| 21 | Saline | 0.84 × 10⁵ | 1.60 × 10⁵ | 0 |
| 21 | Sample | 4 | 9.6 × 10² | 0 |
| 28 | Saline | 1.08 × 10⁵ | 0.84 × 10⁵ | 0 |
| 28 | Sample | 2.0 × 10¹ | 3.64 × 10³ | 0 |
| % viable after 28 days | | 0.018% | 0.29% | 0 |

| Trial 3: MDP + 25 μg BAC | | | |
|---|---|---|---|
| Organism | Original Inoculum (cfu/ml) | Dilution Needed | Adjusted Cell Suspension (cfu/ml) |
| Aspergillis niger (ATCC 16404) | 1.80 × 10⁵ | — | 1.80 × 10⁵ |
| Candida albicans (ATCC 10231) | 1.56 × 10⁶ | — | 1.56 × 10⁶ |
| Staphyloccocus aureus (ATCC 6538) | 5.88 × 10⁷ | 1/10 | 5.88 × 10⁶ |

(10 ml volume) (0.1 ml of the adjusted cell suspension were added to each of 20 ml of the product. Product on test was stored at 20° C.)

| Day | | Aspergillis Niger (cfu/ml) | Candida Albicans (cfu/ml) | Staphylococcus Aureus (cfu/ml) |
|---|---|---|---|---|
| 0 | Saline | 1.76 × 10⁵ | 1.76 × 10⁶ | 2.08 × 10⁷ |
| 0 | Sample | 0.92 × 10⁵ | 1.44 × 10⁶ | 2.84 × 10⁶ |
| 7 | Saline | 1.28 × 10⁵ | 6.96 × 10⁵ | 8.0 × 10⁵ |
| 7 | Sample | 28 | 1.12 × 10² | 0 |
| 14 | Saline | 0.96 × 10⁵ | 3.72 × 10⁵ | 0 |
| 14 | Sample | 24 | 8 | 0 |
| 21 | Saline | 0.84 × 10⁵ | 1.60 × 10⁵ | 0 |

-continued

| | | | | |
|---|---|---|---|---|
| 21 | Sample | $1.08 \times 10^2$ | 4 | 0 |
| 28 | Saline | $1.08 \times 10^5$ | $0.84 \times 10^5$ | 0 |
| 28 | Sample | $1.76 \times 10^2$ | 0 | 0 |
| % viable after 28 days | | 0.19% | 0% | 0 |

Trial 4: MDP + 50 μg BAC

| Organism | Original Inoculum (cfu/ml) | Dilution Needed | Adjusted Cell Suspension (cfu/ml) |
|---|---|---|---|
| Aspergillis niger (ATCC 16404) | $1.80 \times 10^5$ | — | $1.80 \times 10^5$ |
| Candida albicans (ATCC 10231) | $1.56 \times 10^6$ | — | $1.56 \times 10^6$ |
| Staphyloccocus aureus (ATCC 6538) | $5.88 \times 10^7$ | 1/10 | $5.88 \times 10^6$ |

(10 ml volume) (0.1 ml of the adjusted cell suspension were added to each of 20 ml of the product. Product on test was stored at 20° C.)

| Day | | Aspergillis Niger (cfu/ml) | Candida Albicans (cfu/ml) | Staphylococcus Aureus (cfu/ml) |
|---|---|---|---|---|
| 0 | Saline | $1.76 \times 10^5$ | $1.76 \times 10^6$ | $2.08 \times 10^7$ |
| 0 | Sample | $0.68 \times 10^5$ | $8.0 \times 10^5$ | $1.36 \times 10^3$ |
| 7 | Saline | $1.28 \times 10^5$ | $6.96 \times 10^5$ | $8.0 \times 10^5$ |
| 7 | Sample | 0 | 24 | 0 |
| 14 | Saline | $0.96 \times 10^5$ | $3.72 \times 10^5$ | 0 |
| 14 | Sample | 0 | 8 | 0 |
| 21 | Saline | $0.84 \times 10^5$ | $1.60 \times 10^5$ | 0 |
| 21 | Sample | $7.2 \times 10^1$ | 0 | 0 |
| 28 | Saline | $1.08 \times 10^5$ | $0.84 \times 10^5$ | 0 |
| 28 | Sample | $3.6 \times 10^1$ | 0 | 0 |
| % viable after 28 days | | 0.052% | 0% | 0 |

EXAMPLE 7

MDP/PABA/BAC Lyophilized Batch

Two batches of MDP/PABA with benzalkonium chloride were prepared and lyophilized. Two formulations of MDP/PABA/BAC (10 and 25 μg benzalkonium chloride per vial) were prepared. This test was designed to evaluate the lyophilized product for radiolabelling (stress and non-stressed), physical appearance, reconstitution and presence of colloid. The preparations were made as follows: 10 mg MDP, 1 mg $Sn^{2+}$ and 2 mg PABA per vial.

Prep #1: To 50 mL of purged Millex water was added 1 g of MDP. Next was added 2.5 ml of 0.6N HCl containing 100 mg of stannous chloride dihydrate. The pH was adjusted to 7.0. After 5 minutes, added 200 mg/10 mL of PABA already adjusted to pH 7.0. Then was added 1.0 mg/0.1 mL of a solution of benzalkonium chloride. The pH remained at 7.0. Q.S. ed to 100 mL, filtered and dispensed 1 mL per vial.

Prep #2: Repeated the same procedure as Prep #1 but used 2.5 mg/0.25 mL of the benzalkonium chloride solution.

After lyophilization, the two formulations reconstituted well with no sign of colloid. A solid white plug was obtained. The radiochemical labelling was performed on two vials from each formulation. One vial was reconstituted with 200 mCi/5 mL, the other was reconstituted with 200 mCi/(10-7) mL. The same was repeated for the second formulation. The vials were kept at room temperature for the length of the test. The radiolabelling results are tabulated in the following table:

| Percent free Pertechnetate (Room Temperature) | | | | |
|---|---|---|---|---|
| | 10 μg Benzalkonium Cl | | 25 μg Benzalkonium Cl | |
| Time PR | Regular | Stressed | Regular | Stressed |
| 0.5 Hr | <1 | <1 | <1 | <1 |
| 4.0 Hr | <1 | <1 | <1 | <1 |
| 24 Hr | <1 | <1 | <1 | <1 |

In conclusion, both formulations showed excellent stability, even after 24 hours.

EXAMPLE 8

MDP/PABA/BAC Stability of Lyophilized Batches

Two MDP/PABA batches were prepared containing 10 μg and 25 μg respectively, of benzalkonium chloride (see Example 7). The formulations were examined in an accelerated stability study which was conducted according to FDA guidelines. The two batches were kept at both: 22° C. and ambient relative humidity, and at 40° C. and 75% relative humidity for 1 month. The accelerated conditions (40° C. and 75% relative humidity for 1 month) correspond to 8 months under ambient conditions.

Labelling Efficiency

The stress test for labelling efficiency was performed on three vials from each batch, which were stored at 40° C. and 75% R.H.

The labelling test was performed at 30 minutes and at 24 hours post-reconstitution. From 30 minutes to 24 hours, for all three vials of each batch tested, there was <1% free pertechnetate, and <1% reduced hydrolyzed technecium detected.

Biodistribution

Biodistribution tests were performed at 30 minutes and 24 hours post-labelling for each batch of MDP/PABA/BAC.

Standard MDP protocol for biotests was followed. Results were as follows:

| | ANIMAL #1 | ANIMAL #2 | ANIMAL #3 | AVERAGE |
|---|---|---|---|---|
| 10 μg BAC | % ID/ORGAN (30 Min. Post-Labelling) | | | |
| BLOOD | 0.3 | 0.3 | 0.3 | 0.3 |
| LIVER | 0.1 | 0.1 | 0.1 | 0.1 |
| KIDNEYS | 0.6 | 0.6 | 0.4 | 0.5 |
| STOMACH + PI | 0.1 | 0.5 | 0.1 | 0.2 |
| MUSCLE | 0.5 | 0.6 | 0.5 | 0.5 |
| BONE | 62.3 | 55.6 | 58.0 | 58.6 |
| 10 μg BAC | % ID/ORGAN (24 hours Post-Labelling) | | | |
| BLOOD | 0.3 | 0.4 | 0.3 | 0.3 |
| LIVER | 0.1 | 0.2 | 0.1 | 0.1 |
| KIDNEYS | 1.0 | 0.6 | 0.4 | 0.7 |
| STOMACH + PI | 0.1 | 0.2 | 0.1 | 0.1 |
| MUSCLE | 1.1 | 1.3 | 0.8 | 1.1 |
| BONE | 65.6 | 59.2 | 51.1 | 58.6 |
| 25 μg BAC | % ID/ORGAN (30 Min. Post-Labelling) | | | |
| BLOOD | 0.3 | 0.3 | 0.3 | 0.3 |
| LIVER | 0.1 | 0.1 | 0.1 | 0.1 |
| KIDNEYS | 0.4 | 0.5 | 0.4 | 0.4 |
| STOMACH + PI | 0.1 | 0.1 | 0.1 | 0.1 |
| MUSCLE | 0.2 | 0.4 | 0.3 | 0.3 |
| BONE | 55.4 | 59.1 | 54.8 | 56.5 |
| 25 μg BAC | % ID/ORGAN (24 hours Post-Labelling) | | | |
| BLOOD | 0.1 | 0.2 | 0.6 | 0.3 |
| LIVER | 0.1 | 0.1 | 0.1 | 0.1 |
| KIDNEYS | 0.5 | 0.4 | 0.4 | 0.4 |
| STOMACH + PI | 0.1 | 0.1 | 0.1 | 0.1 |

-continued

| | ANIMAL #1 | ANIMAL #2 | ANIMAL #3 | AVERAGE |
|---|---|---|---|---|
| MUSCLE | 0.5 | 0.6 | 0.5 | 0.5 |
| BONE | 60.2 | 44.4 | 59.3 | 54.6 |

The MDP/PABA/BAC vials which had been stored for one month, at 40° C. and 75% relative humidity, performed normally (even after room temperature storage for 24 hours post-reconstitution). This accelerated stability study demonstrated that benzalkonium chloride does not diminish the shelf life of unreconstituted products.

While the foregoing specification teaches the principles of the present invention, with examples provided for the purpose of illustration, it will be understood that the practice of the invention encompasses all of the casual variations, adaptations, modifications, deletions, or additions of procedures and protocols described herein, as come within the scope of the following claims and its equivalents.

What is claimed is:

1. A radiopharmaceutical composition comprising:
   (a) a $^{99m}$Tc-based radiopharmaceutical;
   (b) a water-soluble pertechnetate reducing agent;
   (c) a radical-scavenging antioxidant; and
   (d) a bacteriostat selected from:
      (i) benzalkonium chloride, and
      (ii) benzethonium chloride.

2. The radiopharmaceutical composition of claim 1 wherein the bacteriostat is benzethonium chloride.

3. The radiopharmaceutical composition of claim 1 wherein the radical-scavenging antioxidant is selected from the group consisting of:
   para-aminobenzoic acid;
   gentisic acid; and
   ascorbic acid.

4. A method of administering a radiopharmaceutical agent to a subject, which comprises administering an effective amount of the radiopharmaceutical composition of claim 1 by intravenous, oral, or nebular administration.

5. The radiopharmaceutical composition of claim 1 wherein the bacteriostat is benzalkonium chloride.

6. The radiopharmaceutical composition of claim 5 wherein the water-soluble pertechnetate reducing agent is stannous chloride.

7. The radiopharmaceutical composition of claim 6 wherein the radical-scavenging antioxidant is para-aminobenzoic acid.

8. The radiopharmaceutical composition of claim 7 wherein the $^{99m}$Tc-based radiopharmaceutical is $^{99m}$Tc-methylene-disphosphonic acid or a pharmaceutically acceptable salt thereof.

9. The radiopharmaceutical composition according to claim 1, wherein (d) is present in a concentration from about 0.00001% to about 0.01% (w/v).

10. The radiopharmaceutical composition according to claim 9, wherein (d) is present in a concentration from about 0.00005% to about 0.001% (w/v).

11. The radiopharmaceutical composition according to claim 10, wherein (d) is present in a concentration from about 0.0001% to about 0.0005% (w/v).

12. The radiopharmaceutical compostion of claim 1 wherein the $^{99m}$Tc-based radiopharmaceutical is selected from the group consisting of:
   $^{99m}$Tc-methylene-disphosphonic acid;
   $^{99m}$Tc-hydroxymethylene-diphosphonic acid;
   $^{99m}$Tc-ethane-1-hydroxy-1,1-diphosphonic acid;
   $^{99m}$Tc-1-hydroxypropane-1,1-diphosphonic acid;
   $^{99m}$Tc-2,3-dicarboxypropane-1,1-diphosphonic acid;
   $^{99m}$Tc-pyrophosphate;
   $^{99m}$Tc-trimetaphosphate;
   $^{99m}$Tc-diethylenetriaminepentaacetic acid;
   $^{99m}$Tc-2,3-dimercaptosuccinic acid;
   $^{99m}$Tc-glycero-glucoheptanoic acid;
   [N-[N-[N-(mercaptoacetyl)glycyl]glycyl]-glycinato(5-)-N,N',N",S]-oxo-[$^{99m}$Tc]technetate(V);
   $^{99m}$Tc-macroaggregated albumin;
   $^{99m}$Tc-albumin colloid;
   $^{99m}$Tc-aggregated human albumin;
   $^{99m}$Tc-recombinant human albumin/human serum albumin in microspherical form;
   $^{99m}$Tc-imminodiphosphonic acid;
   $^{99m}$Tc-[(acac)$_2$en];
   $^{99m}$Tc-hydrophosphonic acid;
   $^{99m}$Tc-monoclonal antibody to fibrin;
   $^{99m}$Tc-monoclonal antibody to myosin;
   $^{99m}$Tc-tissue plasminogen activator;
   hexakis(1-isocyano-2-methoxy-2-methylpropane)-[$^{99m}$Tc]technetium(I);
   bis[(1,2-cyclohexanedionedioximato)-(1-)-O]-[(1,2-cyclohexanedionedioximato)-(2-)-O]-methyl-borato-(2-)-N,N',N",N"',N"",N""'-chloro[$^{99m}$Tc]technetium (III);
   ]bis(2,3-butanedione-dioximato)(1-)-O]-[(2,3-butanedione-dioximato)(2-)-O]-(2-methylpropyl)borato-(2)-N,N',N",N"',N"",N""'-chloro[$^{99m}$Tc]technetium;
   $^{99m}$Tc-ethyl cystinate dimer;
   $^{99m}$Tc-3,3'-[(2,2-dimethyltrimethylene)diimino]di-2-butanone-dioxime;
   bis[N-[2-[(3-bromo-2,4,6-trimethylphenyl)amino]-2-oxoethyl]-N-(carboxymethyl)-glycyl]-[$^{99m}$Tc]technetium;
   bis[N-[2-[[2,6-bis(1-methylethyl)phenyl]-amino]2-oxoethyl]-N-(carboxymethyl)-glycyl][$^{99m}$Tc]technetium;
   bis[-N-(carboxymethyl)-N-[2-[2,6-dimethylphenyl)-amino]-2-oxoethyl]-glycyl]-[$^{99m}$Tc]technetium; and
   $^{99m}$Tc-polyisohexylcyanoacrylate nanoparticles;
   or a pharmaceutically acceptable salt thereof.

13. The radiopharmaceutical composition of claim 12 wherein the $^{99m}$Tc-based radiopharmaceutical is selected from:
   $^{99m}$Tc-methylene-disphosphonic acid;
   $^{99m}$Tc-hydroxymethylene-diphosphonic acid;
   $^{99m}$Tc-ethane-1-hydroxy-1,1-diphosphonic acid;
   $^{99m}$Tc-1-hydroxypropane-1,1-diphosphonic acid;
   $^{99m}$Tc-2,3-dicarboxypropane-1,1-diphosphonic acid;
   $^{99m}$Tc-pyrophosphate; and
   $^{99m}$Tc-trimetaphosphate;
   or a pharmaceutically acceptable salt thereof.

14. A method for bone scintigraphy in a subject, which comprises administering an effective amount of the radiopharmaceutical composition of claim 13 by intravenous administration.

15. The radiopharmaceutical composition of claim 12 wherein the $^{99m}$Tc-based radiopharmaceutical is selected from:
   $^{99m}$Tc-diethylenetriaminepentaacetic acid;
   $^{99m}$Tc-2,3-dimercaptosuccinic acid;
   $^{99m}$Tc-glycero-glucoheptanoic acid; and

[N-[N-[N-(mercaptoacetyl)glycyl]glycyl]-
glycinato(5-)-N,N',N'',S]-oxo-[$^{99m}$Tc]tech-
netate(V);
or a pharmaceutically acceptable salt thereof.

16. A method for radioimaging of the kidney in a subject, which comprises administering an effective amount of the radiopharmaceutical composition of claim 15 by intravenous administration.

17. The radiopharmaceutical composition of claim 12 wherein the $^{99m}$Tc-based radiopharmaceutical is selected from:
$^{99m}$Tc-macroaggregated albumin;
$^{99m}$Tc-albumin colloid;
$^{99m}$Tc-aggregated human albumin; and
$^{99m}$Tc-recombinant human albumin/human serum albumin in microspherical form.

18. A method for radioimaging of the lung in a subject, which comprises administering an effective amount of the radiopharmaceutical composition of claim 17 by intravenous or nebular administration.

19. The radiopharmaceutical composition of claim 12 wherein the $^{99m}$Tc-based radiopharmaceutical is selected from:
$^{99m}$Tc-imminodiphosphonic acid;
$^{99m}$Tc-[(acac)$_2$en];
$^{99m}$Tc-hydrophosphonic acid;
$^{99m}$Tc-monoclonal antibody to fibrin;
$^{99m}$Tc-monoclonal antibody to myosin;
$^{99m}$Tc-tissue plasminogen activator;
hexakis(1-isocyano-2-methoxy-2-methylpropane)-
[$^{99m}$Tc]technetium(I);
bis[(1,2-cyclohexanedionedioximato)-(1-)-O]-[(1,2-
cyclohexanedionedioximato)-(2-)-O]-methyl-
borato-(2-)-N,N',N'',N''',N'''',N'''''-chloro[$^{99m}$Tc-
]technetium (III); and
$^{99m}$Tc-glycero-glucoheptanoic acid;
or a pharmaceutically acceptable salt thereof.

20. A method for radioimaging of blood pool and myocardial infarct in a subject, which comprises administering an effective amount of the radiopharmaceutical composition of claim 19 by intravenous administration.

21. The radiopharmaceutical composition of claim 12 wherein the $^{99m}$Tc-based radiopharmaceutical is selected from:
$^{99m}$Tc-diethylenetriaminepentaacetic acid;
[bis(2,3-butanedione-dioximato)(1-)-O]-[(2,3-butaned-
ione-dioximato)(2-)-O]-(2-methylpropyl)borato-(2-
)-N,N',N'',N''',N'''',N'''''-chloro[$^{99m}$Tc]tech-
netium;
$^{99m}$Tc-ethyl cystinate dimer; and
$^{99m}$Tc-3,3'-[(2,2-dimethyltrimethylene)diimino]di-2-
butanone-dioxime;
or a pharmaceutically acceptable salt thereof.

22. A method for brain/cerebral perfusion radioimaging in a subject, which comprises administering an effective amount of the radiopharmaceutical composition of claim 21 by intravenous administration.

23. The radiopharmaceutical composition of claim 12 wherein the $^{99m}$Tc-based radiopharmaceutical is selected from:
bis[N-[2-[(3-bromo-2,4,6-trimethylphenyl)amino]-2-
oxoethyl]-N-(carboxymethyl)-glycyl]-[$^{99m}$Tc]tech-
netium;
bis[N-[2-[[2,6-bis(1-methylethyl)phenyl[amino]-2-
oxoethyl]-N-(carboxymethyl)-glycyl]-[$^{99m}$Tc]tech-
netium;
bis[-N-(carboxymethyl)-N-[2-[2,6-dimethylphenyl)-
amino]-2-oxoethyl]-glycyl]-[$^{99m}$Tc]technetium;
and
$^{99m}$Tc-polyisohexylcyanoacrylate nanoparticles;
or a pharmaceutically acceptable salt thereof.

24. A method for radioimaging of the liver, gall bladder, and/or spleen in a subject, which comprises administering an effective amount of the radiopharmaceutical composition of claim 23 by intravenous administration.

* * * * *